United States Patent
Moriya et al.

(10) Patent No.: US 9,283,165 B2
(45) Date of Patent: Mar. 15, 2016

(54) COSMETIC COMPOSITION

(71) Applicant: Shin-Etsu Chemical Co., Ltd., Tokyo (JP)

(72) Inventors: Hiroyuki Moriya, Annaka (JP); Naoki Omura, Tokyo (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/104,613

(22) Filed: Dec. 12, 2013

(65) Prior Publication Data
US 2015/0164763 A1 Jun. 18, 2015

(51) Int. Cl.
| A61K 8/58 | (2006.01) |
| A61K 8/04 | (2006.01) |
| A61Q 1/02 | (2006.01) |
| C08G 77/26 | (2006.01) |
| A61Q 1/10 | (2006.01) |
| A61K 8/89 | (2006.01) |
| A61Q 5/12 | (2006.01) |
| A61Q 19/00 | (2006.01) |
| A61K 8/898 | (2006.01) |

(52) U.S. Cl.
CPC . *A61K 8/585* (2013.01); *A61K 8/04* (2013.01); *A61K 8/89* (2013.01); *A61K 8/898* (2013.01); *A61Q 1/02* (2013.01); *A61Q 1/10* (2013.01); *A61Q 5/12* (2013.01); *A61Q 19/00* (2013.01); *C08G 77/26* (2013.01)

(58) Field of Classification Search
None
See application file for complete search history.

(56) References Cited

U.S. PATENT DOCUMENTS

| 4,431,789 A | 2/1984 | Okazaki et al. |
| 4,698,178 A | 10/1987 | Huttinger et al. |
| 4,994,593 A | 2/1991 | Lin et al. |
| 5,078,988 A | 1/1992 | Lin et al. |
| 7,655,744 B2 | 2/2010 | Miyanaga |
| 2004/0096416 A1 | 5/2004 | Fack et al. |
| 2005/0202054 A1* | 9/2005 | Faryniarz et al. ............. 424/401 |
| 2008/0038360 A1* | 2/2008 | Zukowski et al. ............. 424/490 |
| 2011/0272320 A1* | 11/2011 | Alwattari et al. .......... 206/524.1 |
| 2013/0093110 A1 | 4/2013 | Watanabe et al. |

FOREIGN PATENT DOCUMENTS

| CN | 102504261 | * | 6/2012 |
| JP | 57-149290 A | | 9/1982 |
| JP | 61-90732 A | | 5/1986 |
| JP | 8-268831 A | | 10/1996 |
| JP | 9-278892 A | | 10/1997 |
| JP | 10-316526 A | | 12/1998 |
| JP | 2004-339244 A | | 12/2004 |
| KR | 101094873 | * | 12/2011 |
| WO | WO2012069331 | * | 5/2012 |

OTHER PUBLICATIONS

European Search Report dated May 26, 2015 for EP Application No. 14192901.8.

* cited by examiner

*Primary Examiner* — Jennifer A Berrios
(74) *Attorney, Agent, or Firm* — Birch, Stewart, Kolasch & Birch, LLP

(57) ABSTRACT

A cosmetic composition comprising an aminoalcohol-modified organopolysiloxane as a surfactant has high emulsion stability and offers favorable properties including non-sticky and moist feelings, long lasting quality, and no strange odor release with the lapse of time.

20 Claims, No Drawings

COSMETIC COMPOSITION

TECHNICAL FIELD

This invention relates to a cosmetic composition comprising an aminoalcohol-modified organopolysiloxane as a surfactant.

BACKGROUND ART

Patent Documents 1 to 3 propose the use of silicone surfactants in emulsion cosmetics, especially water-in-oil type emulsion cosmetics. Known silicone surfactants include polyether-modified silicones (Patent Documents 1 and 2) and polyglycerol-modified silicones (Patent Documents 3 to 6). Emulsion cosmetics having polyether-modified silicones compounded therein are undesirably sticky or greasy even after application. Polyglycerol-modified silicones are improved in the sticky feel inherent to polyether-modified silicones, but still lack emulsion stability. These silicone surfactants are manufactured by adding a hydrophilic compound having a terminal double bond to a silicone having silicon-hydrogen bonds. In the products, a fraction of the hydrophilic compound is inevitably left as impurity. The presence of the residual hydrophilic compound can adversely affect the emulsion stability and lasting quality of cosmetics. Another problem is that such cosmetics will give off a strange odor with the lapse of time.

CITATION LIST

Patent Document 1: JP-A S61-90732 (U.S. Pat. No. 4,698, 178)
Patent Document 2: JP-A H08-268831
Patent Document 3: JP-A H09-278892
Patent Document 4: JP-A S57-149290 (U.S. Pat. No. 4,431, 789)
Patent Document 5: JP-A H10-316526
Patent Document 6: JP-A 2004-339244 (U.S. Pat. No. 7,655, 744)

DISCLOSURE OF INVENTION

An object of the invention is to provide a cosmetic composition comprising an aminoalcohol-modified organopolysiloxane which is substantially free of hydrophilic impurities, as a surfactant, and having high emulsion stability and offering favorable properties including non-sticky and moist feelings, long lasting quality, and no strange odor release with the lapse of time.

The inventors have succeeded in stabilizing an emulsified cosmetic composition by using an aminoalcohol-modified organopolysiloxane of specific structure as a surfactant. The resulting cosmetic composition offers favorable properties including non-sticky and moist feelings, long lasting quality, and no strange odor release with the lapse of time.

The aminoalcohol-modified organopolysiloxane used herein is easier to synthesize and less expensive than the prior art polyether and polyglycerol-modified silicones.

Accordingly, the invention provides a cosmetic composition comprising an aminoalcohol-modified organopolysiloxane as a surfactant, the aminoalcohol-modified organopolysiloxane having a backbone composed of organopolysiloxane segments, at least one silicon atom in the organopolysiloxane segment having bonded thereto a substituent group of the general formula (1):

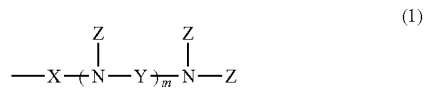

wherein X and Y are each independently a divalent hydrocarbon group of 1 to 10 carbon atoms, m is an integer of 0 to 4, and Z is independently a group selected from hydrogen, alkyl of 1 to 16 carbon atoms, and phenyl, or a group selected from —CH$_2$—CH$_2$—OH, —CH$_2$—CH(OH)—CH$_3$, and —CH$_2$—CH(OH)—CH$_2$—OH, at least 10 mol % of the entire substituent groups represented by Z being the group selected from —CH$_2$—CH$_2$—OH, —CH$_2$—CH(OH)—CH$_3$, and —CH$_2$—CH(OH)—CH$_2$—OH.

In a preferred embodiment, the aminoalcohol-modified organopolysiloxane has the general formula (2):

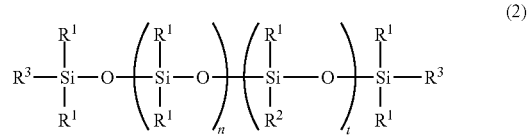

wherein $R^1$ is each independently a group selected from hydrogen, hydroxyl, alkoxy of 1 to 3 carbon atoms, alkyl of 1 to 16 carbon atoms, and phenyl, at least one of $R^2$ and $R^3$ is a group of formula (1), the remainder is a group selected from hydrogen, hydroxyl, alkoxy of 1 to 3 carbon atoms, alkyl of 1 to 16 carbon atoms, and phenyl, n is an integer of 0 to 10,000, and t is an integer of 0 to 100.

If desired, the cosmetic composition further comprises a silicone oil and/or a non-emulsifiable silicone elastomer.

Advantageous Effects of Invention

The cosmetic composition of the invention has high emulsion stability and offers favorable properties including non-sticky and moist feelings, long lasting quality, and no strange odor release with the lapse of time.

DESCRIPTION OF PREFERRED EMBODIMENTS

The cosmetic composition of the invention comprises an aminoalcohol-modified organopolysiloxane as a surfactant. The aminoalcohol-modified organopolysiloxane has a backbone composed of organopolysiloxane segments, wherein at least one silicon atom in the organopolysiloxane segment has a substituent group of the general formula (1) bonded thereto.

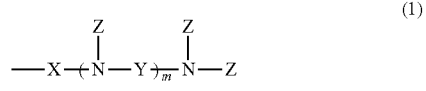

Herein X and Y are each independently a divalent hydrocarbon group of 1 to 10 carbon atoms, m is an integer of 0 to 4, and Z is independently a group selected from hydrogen, alkyl of 1 to 16 carbon atoms, and phenyl, or a group selected from —CH$_2$—CH$_2$—OH, —CH$_2$—CH(OH)—CH$_3$, and —CH$_2$—CH(OH)—CH$_2$—OH, at least 10 mol % of the entire substituent groups represented by Z being the group selected from —CH$_2$—CH$_2$—OH, —CH$_2$—CH(OH)—CH$_3$, and —CH$_2$—CH(OH)—CH$_2$—OH.

In formula (1), X and Y are each independently a divalent hydrocarbon group of 1 to 10 carbon atoms. The preferred groups include linear or branched, divalent aliphatic hydrocarbon groups of 1 to 10 carbon atoms and divalent aromatic hydrocarbon groups of 6 to 10 carbon atoms, more preferably alkylene and alkenylene groups of 1 to 10 carbon atoms, especially 2 to 6 carbon atoms, and phenylene groups. Specifically, ethylene, ethylenylene, trimethylene, propylene, butylene, isobutylene, hexamethylene, and phenylene are preferred. The subscript m is an integer of 0 to 4, preferably 0, 1 or 2. Preferred groups of Z include hydrogen, methyl, ethyl, propyl, butyl, pentyl, hexyl, heptyl, octyl, nonyl, decyl, lauryl, phenyl, —CH$_2$—CH$_2$—OH, —CH$_2$—CH(OH)—CH$_3$, and —CH$_2$—CH(OH)—CH$_2$—OH. More preferably Z is hydrogen, —CH$_2$—CH$_2$—OH or —CH$_2$—CH(OH)—CH$_3$. The group selected from —CH$_2$—CH$_2$—OH, —CH$_2$—CH(OH)—CH$_3$, and —CH$_2$—CH(OH)—CH$_2$—OH should account for at least 10 mol %, preferably at least 50 mol %, and most preferably at least 80 mol % of the entire substituent groups of Z.

The preferred aminoalcohol-modified organopolysiloxane has the general formula (2).

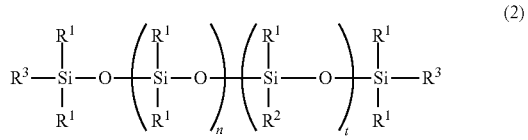

(2)

Herein R$^1$ is each independently a group selected from hydrogen, hydroxyl, alkoxy of 1 to 3 carbon atoms, alkyl of 1 to 16 carbon atoms, and phenyl; at least one of R$^2$ and R$^3$ is a group of formula (1), and the remainder is a group selected from hydrogen, hydroxyl, alkoxy of 1 to 3 carbon atoms, alkyl of 1 to 16 carbon atoms, and phenyl; n is an integer of 0 to 10,000, and t is an integer of 0 to 100.

In formula (2), R$^1$ is each independently a group selected from hydrogen, hydroxyl, alkoxy of 1 to 3 carbon atoms, alkyl of 1 to 16 carbon atoms, and phenyl. Suitable groups include hydrogen, hydroxyl, methoxy, ethoxy, propoxy, isopropoxy, alkyl groups such as methyl, ethyl, propyl, butyl, pentyl, hexyl, heptyl, octyl, nonyl, decyl, cetyl, cyclopentyl, cyclohexyl, and phenyl. Preferred groups include hydroxyl, methoxy, ethoxy, propoxy, isopropoxy, methyl, ethyl, propyl, butyl, pentyl, hexyl, heptyl, octyl, nonyl, decyl, cetyl, and phenyl. Methyl is most preferred. At least one of R$^2$ and R$^3$ is a group of formula (1), while the remainder, if any, is a group selected from hydrogen, hydroxyl, alkoxy of 1 to 3 carbon atoms, alkyl of 1 to 16 carbon atoms, and phenyl, examples of which are as exemplified above for R$^1$. The subscript n is an integer of 0 to 10,000, preferably 10 to 5,000, and more preferably 10 to 1,000; and t is an integer of 0 to 100, preferably 1 to 50, and more preferably 3 to 20.

The aminoalcohol-modified organopolysiloxane used herein may be prepared by the method of JP-A H02-200618. It may be obtained from reaction of an amino-containing organopolysiloxane with ethylene oxide, propylene oxide or glycidol. The unreacted ethylene oxide or propylene oxide may be readily removed by heating and stirring in vacuum at a temperature of 120° C. or higher, or by bubbling nitrogen or the like.

In the cosmetic composition, the aminoalcohol-modified organopolysiloxane is preferably compounded in an amount of 0.1 to 50% by weight based on the total weight of the cosmetic composition although the amount varies with the type and form of the cosmetic composition.

Preferably, the cosmetic composition contains a silicone oil in addition to the aminoalcohol-modified organopolysiloxane. Preferred examples of the silicone oil include dimethylpolysiloxane, methylphenylpolysiloxane, methyltrimethicone, phenyltrimethicone, decamethylcyclopentasiloxane, dodecamethylcyclohexasiloxane, octamethyltrisiloxane, decamethyltetrasiloxane, dodecamethylpentasiloxane, heptamethylethyltrisiloxane, caprylylmethicone, and tetrakistrimethylsiloxysilane. The inclusion of a silicone oil enhances the stability of an emulsified composition and render it less sticky or less greasy. Silicone oils may be used alone or in admixture of two or more. The silicone oil is preferably compounded in an amount of 2 to 40%, more preferably 5 to 20% by weight based on the total weight of the cosmetic composition. Outside the range, emulsion stability may be somewhat compromised.

Also preferably the cosmetic composition may further contain a non-emulsifiable silicone elastomer. The non-emulsifiable silicone elastomer is preferably an elastomer which swells due to inclusion of a low-viscosity silicone having a kinematic viscosity of 0.65 to 10.0 mm$^2$/sec at 25° C. as measured by an Ostwald's viscometer, in an amount more than its own weight. The non-emulsifiable silicone elastomer preferably has a crosslinking structure formed by reaction of a crosslinking agent having at least two vinyl reactive sites in the molecule with silicon-bonded hydrogen atoms. Furthermore, the non-emulsifiable silicone elastomer preferably has a moiety of at least one type selected from among alkyl, alkenyl, aryl, and fluoroalkyl moieties. When used, the non-emulsifiable silicone elastomer is preferably compounded in an amount of 0.1 to 30%, more preferably 1 to 10% by weight based on the total weight of the cosmetic composition.

Suitable non-emulsifiable silicone elastomers are commercially available, for example, dimethicone/vinyldimethicone cross-polymers KSG-15 and KSG-16, dimethicone/phenylvinyldimethicone cross-polymers KSG-18, etc., vinyldimethicone/lauryldimethicone cross-polymers KSG-41, etc., all from Shin-Etsu Chemical Co., Ltd., and dimethicone cross-polymers (designated by INCI). Other examples include dimethicone/vinyldimethicone cross-polymers KMP-400, etc. and vinyldimethicone/methiconesilsesquioxane cross-polymers KSP-10, etc., all available from Shin-Etsu Chemical Co., Ltd. The inclusion of a non-emulsifiable silicone elastomer enhances the stability of an emulsified composition and provides it with non-stickiness, long lasting quality and moist feeling.

To the cosmetic composition, any ingredients commonly used in ordinary cosmetics may be added. Suitable ingredients include solid, semisolid or liquid oils, water, alcohols, water-soluble polymers, film-forming agents, surfactants, oil-soluble gelling agents, organic modified clay minerals, resins, powders, UV absorbers, humectants, preservatives, antifungal agents, perfumes, salts, antioxidants, pH modifiers, chelating agents, refreshing agents, anti-inflammatory agents, skin conditioning agents, vitamins, amino acids, nucleic acids, hormones, and inclusions. Illustrative examples are given below, but not limited thereto.

Suitable alcohols which can be used herein include ethanol, propanol, ethylene glycol, ethylene glycol monoalkyl ethers, diethylene glycol monoethyl ether, polyethylene glycol, propylene glycol, dipropylene glycol, 1,3-butylene glycol, glycerol, diglycerol, polyglycerol, pentaerythritol, sucrose, lactose, xylitol, sorbitol, mannitol, maltitol, carrageenan, agar, guar gum, dextrin, tragacanth gum, locust bean gum, polyvinyl alcohol, polyoxyethylene base polymers, polyoxyethylene-polyoxypropylene copolymers, hyaluronic acid, chondroitin sulfate, chitin, and chitosan, which may be used alone or in admixture of two or more. The alcohol is preferably compounded in an amount of 0.1 to 90.0%, more preferably 0.5 to 50.0% by weight of the cosmetic composition. Less than 0.1 wt % of the alcohol is insufficient for humectant, antifungal and antibacterial effects. More than 90.0 wt % of the alcohol may prevent the cosmetic composition from exerting the desired effects.

Suitable oils which can be used herein are exemplified below. Note that POE stands for polyoxyethylene. Naturally occurring animal/plant oils and fats and semi-synthetic oils include avocado oil, linseed oil, almond oil, insect wax, perilla oil, olive oil, cacao butter, kapok oil, kaya oil, carnauba wax, liver oil, candelilla wax, beef tallow, beef foot oil, beef bone fat, hydrogenated beef tallow, persic oil, spermaceti, hydrogenated oil, wheat germ oil, sesame oil, rice germ oil, rice bran oil, sugar cane wax, sasanqua oil, safflower oil, shea butter, Chinese tung oil, cinnamon oil, jojoba oil, shellac wax, turtle oil, soybean oil, tea seed oil, tsubaki oil, evening primrose oil, corn oil, lard, rape oil, Japanese tung oil, rice bran wax, germ oil, horse fat, palm oil, palm kernel oil, castor oil, hydrogenated castor oil, castor oil fatty acid methyl ester, sunflower oil, grape seed oil, bay oil, macadamia nut oil, bees wax, mink oil, cotton seed oil, cotton wax, haze tallow, haze kernel oil, montan wax, coconut oil, hydrogenated coconut oil, tri-coconut oil fatty acid glyceride, mutton tallow, peanut oil, lanolin, liquid lanolin, reduced lanolin, lanolin alcohol, hard lanolin, lanolin acetate, lanolin fatty acid isopropyl, POE lanolin alcohol ether, POE lanolin alcohol acetate, lanolin fatty acid polyethylene glycol, POE hydrogenated lanolin alcohol ether, and egg yolk oil.

Suitable hydrocarbon oils include ozokerite, squalane, squalene, ceresin, paraffin, paraffin wax, isodecane, isododecane, isohexadecane, liquid paraffin, pristane, polyisobutylene, microcrystalline wax, and vaseline. Suitable higher fatty acids include lauric acid, myristic acid, palmitic acid, stearic acid, behenic acid, undecylenic acid, oleic acid, linoleic acid, linolenic acid, arachidic acid, eicosapentaenoic acid, docosahexaenoic acid, isostearic acid, and 12-hydroxystearic acid.

Suitable higher alcohols include lauryl alcohol, myristyl alcohol, palmityl alcohol, stearyl alcohol, behenyl alcohol, hexadecyl alcohol, oleyl alcohol, isostearyl alcohol, hexyl dodecanol, octyl dodecanol, sedostearyl alcohol, 2-decyltetradecinol, cholesterol, phytosterol, POE cholesterol ether, monostearyl glycerol ether (or batyl alcohol), and monooleyl glycerol ether (or selachyl alcohol).

Suitable ester oils include diisobutyl adipate, 2-hexyldecyl adipate, di-2-heptylundecyl adipate, N-alkylglycol monoisostearate, isocetyl isostearate, trimethylol propane triisostearate, ethylene glycol di-2-ethylhexanoate, neopentyl glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dicaprylate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isononyl isononanoate, triisohexanoin, isopropyl myristate, 2-octyldodecyl myristate, 2-hexyldecyl myristate, myristyl myristate, hexyldecyl dimethyloctanoate, ethyl laurate, hexyl laurate, 2-octyldecyl N-lauroyl-L-glutamate, diisostearyl malate, dextrin palmitate, dextrin stearate, dextrin 2-ethylhexanoate/palmitate, sucrose palmitate, sucrose stearate, monobenzolidene sorbitol, and dibenzylidene sorbitol.

Suitable glyceride oils include acetoglyceride, glyceryl diisooctanoate, glyceryl triisostearate, glyceryl triisopalmitate, glyceryl tri-2-ethylhexanoate, glyceryl monostearate, glyceryl di-2-heptylundecanoate, and glyceryl trimyristate.

These oils may be used alone or in admixture of two or more. The oil is preferably compounded in an amount of 0 to 90%, more preferably 1 to 90% by weight of the cosmetic composition. When the cosmetic composition contains water, the amount of water used is preferably 1 to 99% by weight. Although the cosmetic composition may be prepared to appropriate properties by combining the foregoing ingredients, any of the following ingredients i), ii) and iii) may be added if desired.

i) Powder and/or Colorant

Suitable inorganic powders include titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, lepidolite, biotite, silicic acid, silicic anhydride, aluminum silicate, magnesium silicate, aluminum magnesium silicate, calcium silicate, barium silicate, strontium silicate, metal tungstates, hydroxyapatite, vermiculite, Higilite®, bentonite, montmorillonite, hectorite, zeolite, ceramic powder, calcium secondary phosphate, alumina, aluminum hydroxide, boron nitride, and silica.

Suitable organic powders include polyamide powder, polyester powder, polyethylene powder, polypropylene powder, polystyrene powder, polyurethane powder, benzoguanamine powder, polymethyl benzoguanamine powder, tetrafluoroethylene powder, polymethyl methacrylate powder, cellulose powder, silk powder, nylon powder such as 12-nylon or 6-nylon, and powder forms of styrene-acrylic acid copolymers, divinylbenzene-styrene copolymers, vinyl resins, urea resins, phenolic resins, fluoro-resins, silicone resins, acrylic resins, melamine resins, epoxy resins, polycarbonate resins, microcrystalline fiber powder, starch, and lauroyl lysine.

Suitable surfactant metal salt powders (metal soaps) include zinc stearate, aluminum stearate, calcium stearate, magnesium stearate, zinc myristate, magnesium myristate, zinc cetyl phosphate, calcium cetyl phosphate, and zinc sodium cetyl phosphate.

Suitable colored pigments include inorganic red pigments such as iron oxide, iron hydroxide and iron titanate, inorganic brown pigments such as γ-iron oxide, inorganic yellow pigments such as yellow iron oxide and ochre, inorganic black pigments such as black iron oxide and carbon black, inorganic purple pigments such as manganese violet and cobalt violet, inorganic green pigments such as chromium hydroxide, chromium oxide, cobalt oxide, and cobalt titanate, inorganic blue pigments such as Prussian blue and ultramarine, lake-form tar dyes, lake-form natural dyes, and composite powders obtained by combining the foregoing.

Suitable pearlescent pigments include titania-coated mica, bismuth oxychloride, titania-coated bismuth oxychloride, titania-coated talc, fish scales flake, and titania-coated colored mica. Suitable metal powder pigments include aluminum powder, copper powder and stainless steel powder.

Suitable tar dyes include Red #3, Red #104, Red #106, Red #201, Red #202, Red #204, Red #205, Red #220, Red #226, Red #227, Red #228, Red #230, Red #401, Red #505, Yellow #4, Yellow #5, Yellow #202, Yellow #203, Yellow #204, Yellow #401, Blue #1, Blue #2, Blue #201, Blue #404, Green #3, Green #201, Green #204, Green #205, Orange #201, Orange #203, Orange #204, Orange #206, Orange #207, etc. Suitable natural dyes include carminic acid, laccaic acid, carthamin, brazilin and crocin.

These powders and colorants are not particularly limited in form (spherical, needle or plate), particle size (fumed, microparticulate or pigment grade), and particle structure (porous or nonporous) as long as they are commonly used in cosmetics. Two or more powders may be combined into composite powder. The powders may be surface treated with oils, silicones other than formula (1), or fluorochemical compounds.

ii) Surfactant

Suitable surfactants which can be used herein include saturated or unsaturated fatty acid soaps such as sodium stearate and triethanolamine oleate, alkyl ether carboxylic acids and salts thereof, carboxylic acid salts such as condensates of amino acids and fatty acids, amide ether carboxylic acid salts, α-sulfofatty acid ester salts, α-acylsulfonic acid salts, alkylsulfonic acid salts, alkenesulfonic acid salts, sulfonic acid salts of fatty acid esters, sulfonic acid salts of fatty acid amides, alkylsulfonic acid salts and sulfonic acid salts of formaldehyde condensates thereof, alkylsulfuric acid ester salts, secondary higher alcohol sulfuric acid ester salts, alkyl and allyl ether sulfuric acid ester salts, sulfuric acid ester salts of fatty acid esters, sulfuric acid ester salts of fatty acid alkylol amides, sulfuric acid ester salts of Turkey red oil or the like, alkyl phosphates, alkenyl phosphates, ether phosphoric acid salts, alkyl allyl ether phosphoric acid salts, alkylamide phosphoric acid salts, and N-acylamino acid surfactans.

Cationic surfactants include amine salts such as alkyl amine salts, polyamine and aminoalcohol fatty acid derivatives, alkyl quaternary ammonium salts, aromatic quaternary ammonium salts, pyridinium salts and imidazolium salts.

Nonionic surfactants include sorbitan fatty acid esters, glycerol fatty acid esters, polyglycerol fatty acid esters, propylene glycol fatty acid esters, polyethylene glycol fatty acid esters, sucrose fatty acid esters, polyoxyethylene alkyl ethers, polyoxypropylene alkyl ethers, polyoxyethylene alkyl phenyl ethers, polyoxyethylene fatty acid esters, polyoxyethylene sorbitan fatty acid esters, polyoxyethylene sorbitol fatty acid esters, polyoxyethylene glycerol fatty acid esters, polyoxyethylene propylene glycol fatty acid esters, polyoxyethylene castor oil, polyoxyethylene hydrogenated castor oil, polyoxyethylene phytostanol ether, polyoxyethylene phytosterol ether, polyoxyethylene cholestanol ether, polyoxyethylene cholesteryl ether, polyoxyalkylene-modified organopolysiloxanes, polyoxyalkylene/alkyl-co-modified organopolysiloxanes, polyoxyalkylene/fluoroalkyl-co-modified organopolysiloxanes, polyoxyalkylene-organopolysiloxane block copolymers, alkanolamides, sucrose ethers, and sucrose amides. Ampholytic surfactants include betaine, aminocarboxylic acid salts, and imidazoline derivatives.

iii) Silicone resins such as acrylic-silicone graft or block copolymers and silicone network compounds To the cosmetic composition, at least one silicone resin selected from among acrylic-silicone graft or block copolymers and silicone network compounds may be added for a particular purpose. The silicone resin is preferably an acrylic silicone resin, more preferably an acrylic silicone resin containing in the molecule at least one moiety selected from pyrrolidone, long-chain alkyl, polyoxyalkylene and fluoroalkyl moieties. Also preferably the silicone resin is a silicone network compound. Such a silicone resin is preferably compounded in an amount of 0.1 to 20%, more preferably 1 to 10% by weight based on the total weight of the cosmetic composition.

Preferably the cosmetic composition may be used as skin care, make-up, UV care, anti-perspirant, and hair care cosmetics, for example. The product form is not particularly limited, and such cosmetics may be in liquid, emulsion, cream, solid, paste, gel, powder, multilayer, mousse, spray and other forms.

EXAMPLE

Preparation Examples, Comparative Preparation Examples, Examples, and Comparative Examples are given below by way of illustration and not by way of limitation. Unless otherwise stated, the amount of each ingredient is a neat amount. All parts and % are by weight. Viscosity is measured at 25° C. by Ostwald's viscometer.

Preparation Example 1

A pressure autoclave was charged with 300 parts of amino-modified organopolysiloxane having a viscosity of 60 mm²/sec and an amine equivalent of 2,600 g/mol, represented by the following average compositional formula:

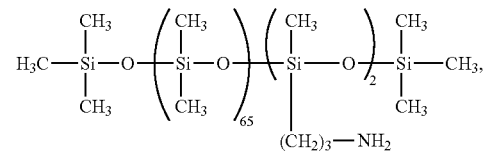

and 30 parts of ethylene oxide, which were stirred at 80° C. for 18 hours. The reaction mixture was stripped under vacuum at 150° C. to remove the unreacted reactants, obtaining a colorless clear liquid having a viscosity of 200 mm²/sec. On $^1$H-NMR analysis (CDCl$_3$, 400 MHz, by Bruker Corp.), it was found that —NH$_2$ group had been converted to —N(CH$_2$—CH$_2$—OH)$_2$.

Preparation Example 2

A pressure autoclave was charged with 200 parts of amino-modified organopolysiloxane having a viscosity of 1,100 mm²/sec and an amine equivalent of 1,580 g/mol, represented by the following average compositional formula:

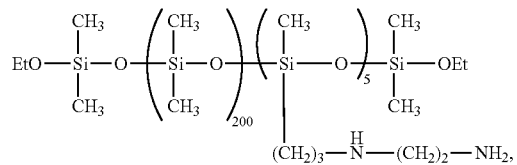

40 parts of 2-propanol, and 70 parts of propylene oxide, which were stirred at 100° C. for 10 hours. The reaction mixture was stripped under vacuum at 150° C. to remove the solvent and unreacted reactants, obtaining a colorless clear liquid having a viscosity of 2,350 mm²/sec. On $^1$H-NMR analysis (CDCl$_3$, 400 MHz, by Bruker Corp.), it was found that —NH— group had been converted to —N[CH$_2$—CH(OH)—CH$_3$]— and —NH$_2$ group had been converted to —N[CH$_2$—CH(OH)—CH$_3$]$_2$.

Preparation Example 3

A pressure autoclave was charged with 100 parts of amino-modified organopolysiloxane having a viscosity of 950 mm²/ sec and an amine equivalent of 850 g/mol, represented by the following average compositional formula:

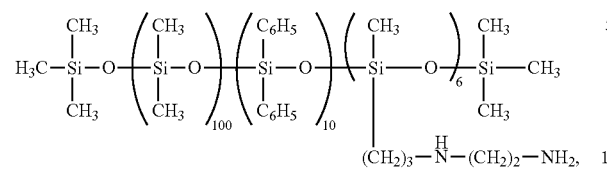

50 parts of 2-propanol, and 75 parts of propylene oxide, which were stirred at 100° C. for 8 hours. The reaction mixture was stripped under vacuum at 150° C. to remove the solvent and unreacted reactants, obtaining a colorless clear liquid having a viscosity of 3,200 mm$^2$/sec. On $^1$H-NMR analysis (CDCl$_3$, 400 MHz, by Bruker Corp.), it was found that —NH— group had been converted to —N[CH$_2$—CH(OH)—CH$_3$]— and —NH$_2$ group had been converted to —N[CH$_2$—CH(OH)—CH$_3$]$_2$.

Preparation Example 4

A pressure autoclave was charged with 500 parts of amino-modified organopolysiloxane having a viscosity of 16,000 mm$^2$/sec and an amine equivalent of 7,500 g/mol, represented by the following average compositional formula:

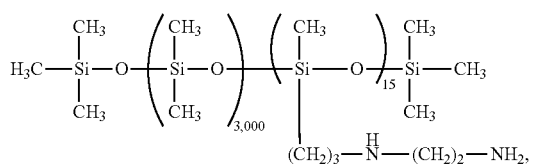

400 parts of 1-butanol, and 100 parts of propylene oxide, which were stirred at 110° C. for 10 hours. The reaction mixture was stripped under vacuum at 150° C. to remove the solvent and unreacted reactants, obtaining a colorless clear liquid having a viscosity of 59,000 mm$^2$/sec. On $^1$H-NMR analysis (CDCl$_3$, 400 MHz, by Bruker Corp.), it was found that —NH— group had been converted to —N[CH$_2$—CH(OH)—CH$_3$]— and —NH$_2$ group had been converted to —N[CH$_2$—CH(OH)—CH$_3$]$_2$.

Preparation Example 5

A pressure autoclave was charged with 500 parts of amino-modified organopolysiloxane having a viscosity of 280 mm$^2$/sec and an amine equivalent of 620 g/mol, represented by the following average compositional formula:

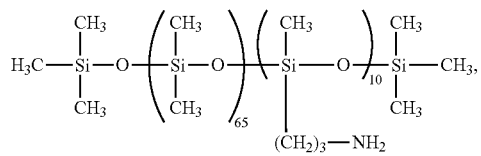

150 parts of 2-propanol, and 12.5 parts of glycidol, which were stirred at 110° C. for 10 hours. The reaction mixture was stripped under vacuum at 150° C. to remove the solvent and unreacted reactants, obtaining a pale yellow, clear liquid having a viscosity of 4,560 mm$^2$/sec. On $^1$H-NMR analysis (CDCl$_3$, 400 MHz, by Bruker Corp.), it was found that 20 mol % of —NH$_2$ groups had been converted to —NH[CH$_2$—CH(OH)—CH$_2$—OH].

Comparative Preparation Example 1

A reactor was charged with 400 parts of methylhydrogenorganopolysiloxane having a viscosity of 78 mm$^2$/sec, represented by the following average compositional formula:

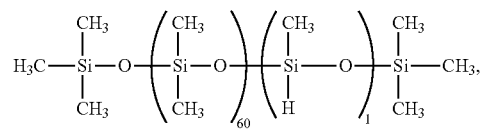

120 parts of 2-propanol, 29 parts of allyl glycerol represented by the following average compositional formula:

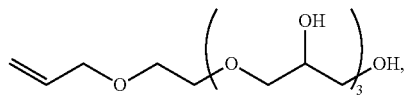

0.02 part of a 1-butanol solution (Pt 3 wt %) of chloroplatinic acid-divinyltetramethyldisiloxane complex, and 0.04 part of 10 wt % ethanol solution of potassium acetate, which were stirred at 80° C. for 5 hours. The solvent was removed from the reaction mixture by stripping under vacuum at 110° C. for 3 hours. There was obtained a colorless, slightly turbid liquid having a viscosity of 3,120 mm$^2$/sec.

Examples 1 to 3 and Comparative Examples 1 to 4

Using the standard technique, several cream samples were prepared according to the formulation of Table 1. The cream samples were examined by the following sensory test.

Sensory Test

A panel of 5 persons made evaluation after a 2-g portion of the cream (Table 1) was applied to the skin and allowed to fully adjust thereto. Evaluated items included non-sticky feeling, moist feeling, lasting of moist feeling, odor and emulsion stability one month after cream preparation. The sample was rated according to the following criterion in terms of the number of panel persons who judged "effective". The results are also shown in Table 1.

Test Criterion

Excellent: 4 or 5 persons answered effective

Good: 3 persons answered effective

Fair: 2 persons answered effective

Poor: 1 or 0 person answered effective

TABLE 1

|  | Ingredients (%) | Example 1 | Example 2 | Example 3 | Comparative Example 1 | Comparative Example 2 | Comparative Example 3 | Comparative Example 4 |
|---|---|---|---|---|---|---|---|---|
| 1. | Aminoalcohol-modified organopolysiloxane in Preparation Example 1 | 3 | | | | | | |
| 2. | Aminoalcohol-modified organopolysiloxane in Preparation Example 2 | | 3 | | | | | |
| 3. | Aminoalcohol-modified organopolysiloxane in Preparation Example 3 | | | 3 | | | | |
| 4. | Glycerol-containing organopolysiloxane in Comparative Preparation Example 1 | | | | 3 | | | |
| 5. | Sofcare GS-G*[1] | | | | | 3 | | |
| 6. | KF-6017*[2] | | | | | | 3 | |
| 7. | KF-6050*[3] | | | | | | | 3 |
| 8. | Dimethylpolysiloxane (6 mm$^2$/sec) | 6 | 6 | 6 | 6 | 6 | 6 | 6 |
| 9. | Squalane | 2 | 2 | 2 | 2 | 2 | 2 | 2 |
| 10. | Mineral oil | 1 | 1 | 1 | 1 | 1 | 1 | 1 |
| 11. | KSG-15*[4] | 8 | 8 | 8 | 8 | 8 | 8 | 8 |
| 12. | 1,3-butylene glycol | 7 | 7 | 7 | 7 | 7 | 7 | 7 |
| 13. | Sodium citrate | 0.2 | 0.2 | 0.2 | 0.2 | 0.2 | 0.2 | 0.2 |
| 14. | Sodium chloride | 0.2 | 0.2 | 0.2 | 0.2 | 0.2 | 0.2 | 0.2 |
| 15. | Ethanol | 4 | 4 | 4 | 4 | 4 | 4 | 4 |
| 16. | Purified water | balance | balance | balance | balance | balance | balance | balance |
|  | Total | 100.0 | 100.0 | 100.0 | 100.0 | 100.0 | 100.0 | 100.0 |
| Evaluation | Non-sticky feeling | Excellent | Excellent | Good | Good | Fair | Fair | Poor |
|  | Moist feeling | Excellent | Good | Excellent | Good | Good | Fair | Poor |
|  | Lasting of moist feeling | Good | Excellent | Excellent | Fair | Fair | Poor | Fair |
|  | Odor @1 month | Good | Excellent | Excellent | Poor | Fair | Good | Fair |
|  | Emulsion stability @1 month | Good | Excellent | Excellent | Fair | Fair | Fair | Fair |

*[1]Sofcare GS-G: glycerol-modified silicone by Kao Corp.
*[2]KF-6017: polyether-modified silicone by Shin-Etsu Chemical Co., Ltd.
*[3]KF-6050: high-degree-of-polymerization polyether-modified silicone by Shin-Etsu Chemical Co., Ltd.
*[4]KSG-15: dimethylpolysiloxane elastomer by Shin-Etsu Chemical Co., Ltd.

Example 4

Using the standard technique, a liquid emulsified foundation was prepared according to the following formulation.

Ingredients

| | Ingredient | Amount |
|---|---|---|
| 1. | Dimethylpolysiloxane (6 mm$^2$/sec) | 5.0 |
| 2. | Squalane | 4.0 |
| 3. | Neopentyl glycol dioctanoate | 3.0 |
| 4. | Myristic acid/isostearic acid diglyceride | 2.0 |
| 5. | α-Monoisostearyl glyceryl ether | 1.0 |
| 6. | Aminoalcohol-modified organopolysiloxane in Preparation Example 2 | 1.0 |
| 7. | Aluminum distearate | 0.2 |
| 8. | Powder dispersion*[5] | 26.2 |
| 9. | Magnesium sulfate | 0.7 |
| 10. | Glycerol | 3.0 |
| 11. | Preservative | appropriate |
| 12. | Perfume | appropriate |
| 13. | Purified water | balance |
| | Total | 100.0% |

*[5]dispersion of aluminum hydroxide and stearic acid-coated titania in decamethylcyclopentasiloxane, SPD-T5 (Shin-Etsu Chemical Co., Ltd.)

The liquid emulsified foundation was found to be lightly spreadable and have better properties including non-sticky (or non-greasy), moist, fresh and light feelings on use, long lasting, and no changes with temperature and time, indicative of stability.

Example 5

Using the standard technique, an eye liner was prepared according to the following formulation.

Ingredients

| | Ingredient | Amount |
|---|---|---|
| 1. | Decamethylcyclopentasiloxane | 22.0 |
| 2. | Dimethylpolysiloxane (6 mm$^2$/sec) | 5.0 |
| 3. | Black iron oxide | 20.0 |
| 4. | Vitamin E acetate | 0.2 |
| 5. | Jojoba oil | 2.0 |
| 6. | Bentonite | 3.0 |
| 7. | Aminoalcohol-modified organopolysiloxane in Preparation Example 1 | 2.0 |
| 8. | Ethanol | 10.0 |
| 9. | 1,3-Butylene glycol | 10.0 |
| 10. | Preservative | appropriate |
| 11. | Perfume | appropriate |
| 12. | Purified water | balance |
| | Total | 100.0% |

The eye liner was found to be lightly spreadable, easily drawable, and have better properties including refreshing, light, non-sticky feelings on use, and no changes with temperature and time, indicating pleasant feel on use and high stability. It also had water resistance, perspiration resistance, and long lasting quality.

Example 6

Using the standard technique, a cosmetic emulsion was prepared according to the following formulation.
Ingredients

| | | |
|---|---|---|
| 1. | Decamethylcyclopentasiloxane | 12.0 |
| 2. | Glyceryl triisooctanoate | 10.0 |
| 3. | Aminoalcohol-modified organopolysiloxane in Preparation Example 4 | 2.0 |
| 4. | Aminoalcohol-modified organopolysiloxane in Preparation Example 1 | 0.2 |
| 5. | Glycerol | 10.0 |
| 6. | Magnesium ascorbate/phosphate | 3.0 |
| 7. | Sodium chloride | 2.0 |
| 8. | Preservative | appropriate |
| 9. | Perfume | appropriate |
| 10. | Purified water | balance |
| | Total | 100.0% |

The emulsion was found to be fine textured, lightly spreadable, and have better properties including non-sticky, moist and fresh feelings on use, and no changes with temperature and time, indicative of high stability.

Example 7

Using the standard technique, a polyhydric alcohol-in-oil emulsified cosmetic was prepared according to the following formulation.
Ingredients

| | | |
|---|---|---|
| 1. | Dimethylpolysiloxane elastomer*6 | 30.0 |
| 2. | Decamethylcyclopentasiloxane | 15.0 |
| 3. | Dimethylpolysiloxane (6 mm²/sec) | 7.0 |
| 4. | Aminoalcohol-modified organopolysiloxane in Preparation Example 5 | 3.0 |
| 5. | Dimethyl distearyl ammonium hectolite | 2.0 |
| 6. | Preservative | appropriate |
| 7. | Perfume | appropriate |
| 8. | Sodium chloride | 0.05 |
| 9. | 1,3-Butylene glycol | balance |
| | Total | 100.0% |

*6 dimethylpolysiloxane elastomer KSG-15 by Shin-Etsu Chemical Co., Ltd.

The emulsified cosmetic was found to be lightly spreadable, and have better properties including non-sticky, non-greasy feelings on use, moist feel on skin, and high stability.

The invention claimed is:

1. A cosmetic composition comprising: an aminoalcohol-modified organopolysiloxane as a surfactant, said aminoalcohol-modified organopolysiloxane having a backbone composed of organopolysiloxane segments, at least one silicon atom in the organopolysiloxane segment having bonded thereto a substituent group of the general formula (1):

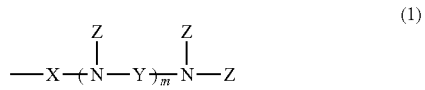

(1)

wherein X and Y are each independently a divalent hydrocarbon group of 1 to 10 carbon atoms, m is an integer of 0 to 4, and Z is independently a group selected from hydrogen, alkyl of 1 to 16 carbon atoms, and phenyl, or a group selected from —CH$_2$—CH$_2$—OH, —CH$_2$—CH(OH)—CH$_3$, and —CH$_2$—CH(OH)—CH$_2$—OH, at least 10 mol % of the entire substituent groups represented by Z being the group selected from —CH$_2$—CH$_2$—OH, —CH$_2$—CH(OH)—CH$_3$, and —CH$_2$—CH(OH)—CH$_2$—OH, and Z comprises only one group selected from —CH$_2$—CH$_2$—OH, —CH$_2$—CH(OH)—CH$_3$, and —CH$_2$—CH(OH)—CH$_2$—OH, wherein said aminoalcohol-modified organopolysiloxane has the general formula (2):

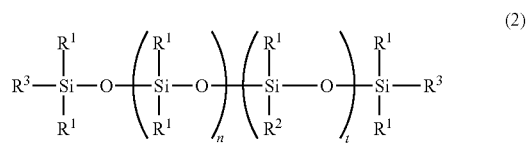

(2)

wherein R$^1$ is each independently a group selected from hydrogen, hydroxyl, alkoxy of 1 to 3 carbon atoms, alkyl of 1 to 16 carbon atoms, and phenyl, R$^2$ is the group of formula (1), R$^3$ is a group selected from hydrogen, hydroxyl, alkoxy of 1 to 3 carbon atoms, alkyl of 1 to 16 carbon atoms, and phenyl, n is an integer of 0 to 10,000, and t is an integer of 1 to 100;

wherein if Z comprises —CH$_2$—CH$_2$—OH, m=0,
if Z comprises —CH$_2$—CH(OH)—CH$_2$—OH, m=0,
if Z comprises —CH$_2$—CH(OH)—CH$_3$,
(i) R$^3$ is alkoxy group of 1 to 3 carbon atoms,
(ii) at least one of R$^1$ if phenyl group, or
(iii) n is an integer of 3,000 to 10,000; and
a cosmetically acceptable ingredient.

2. The cosmetic composition of claim 1, wherein the cosmetically acceptable ingredient is a silicone oil.

3. The cosmetic composition of claim 1, wherein the cosmetically acceptable ingredient is a non-emulsifiable silicone elastomer.

4. The cosmetic composition of claim 1, wherein Z comprises —CH$_2$—CH(OH)—CH$_2$—OH.

5. The cosmetic composition of claim 1, wherein Z comprises —CH$_2$—CH(OH)—CH$_3$.

6. The cosmetic composition of claim 1, wherein Z comprises —CH$_2$—CH$_2$—OH.

7. The cosmetic composition of claim 6, wherein X=(CH$_2$)$_3$, m=0, R$^1$=CH$_3$, and R$^3$=CH$_3$.

8. The cosmetic composition of claim 7, wherein n=65, and t=2.

9. The cosmetic composition of claim 1, wherein Z comprises —CH$_2$—CH(OH)—CH$_3$, and R$^3$ is alkoxy group of 1 to 3 carbon atoms.

10. The cosmetic composition of claim 1, wherein Z comprises —CH$_2$—CH(OH)—CH$_3$, and at least one of R$^1$ is phenyl group.

11. The cosmetic composition of claim 1, wherein Z comprises —CH$_2$—CH(OH)—CH$_3$, and n is an integer of 3,000 to 10,000.

12. The cosmetic composition of claim 1, wherein n is an integer of 10 to 10,000.

13. The cosmetic composition of claim 1, wherein the cosmetically acceptable ingredient is an ingredient selected from the group consisting of powder and colorant.

14. The cosmetic composition of claim 1, wherein the cosmetically acceptable ingredient is an ingredient selected from the group consisting of acrylic-silicone graft copolymers, acrylic-silicone block copolymers and silicone network compounds.

15. The cosmetic composition of claim 1, in the form of a liquid, emulsion, cream, solid, paste, gel, powder, or multi-layer.

16. The cosmetic composition of claim 1, wherein the cosmetically acceptable ingredient is a skin care cosmetic ingredient.

17. The cosmetic composition of claim 1, wherein the cosmetically acceptable ingredient is a make-up cosmetic ingredient.

18. The cosmetic composition of claim 1, wherein the cosmetically acceptable ingredient is a UV care ingredient.

19. The cosmetic composition of claim 1, wherein the cosmetically acceptable ingredient is an anti-perspirant cosmetic ingredient.

20. Method of using the cosmetic composition of claim 1 as a skin care cosmetic ingredient, make-up cosmetic ingredient, UV care ingredient or anti-perspirant cosmetic ingredient comprising applying the cosmetic composition to the skin of a subject.

* * * * *